(12) United States Patent
Siemionow et al.

(10) Patent No.: US 11,315,293 B2
(45) Date of Patent: Apr. 26, 2022

(54) AUTONOMOUS SEGMENTATION OF CONTRAST FILLED CORONARY ARTERY VESSELS ON COMPUTED TOMOGRAPHY IMAGES

(71) Applicant: Kardiolytics Inc., Tulsa, OK (US)

(72) Inventors: Kris Siemionow, Chicago, IL (US); Marek Kraft, Poznan (PL); Dominik Pieczynski, Tulce (PL); Paul Lewicki, Tulsa, OK (US); Zbigniew Malota, Zabrze (PL); Wojciech Sadowski, Zabrze (PL); Jacek Kania, Rogozno (PL)

(73) Assignee: Kardiolytics Inc., Tulsa, OK (US)

( * ) Notice: Subject to any disclaimer, the term of this patent is extended or adjusted under 35 U.S.C. 154(b) by 39 days.

(21) Appl. No.: 16/895,024

(22) Filed: Jun. 8, 2020

(65) Prior Publication Data
US 2020/0320751 A1    Oct. 8, 2020

Related U.S. Application Data

(60) Provisional application No. 62/830,441, filed on Apr. 6, 2019.

(51) Int. Cl.
G06T 11/00 (2006.01)
G06T 7/11 (2017.01)
G06N 3/08 (2006.01)

(52) U.S. Cl.
CPC .............. *G06T 11/005* (2013.01); *G06N 3/08* (2013.01); *G06T 7/11* (2017.01); *G06T 2211/412* (2013.01)

(58) Field of Classification Search
CPC ......... A61B 6/032; A61B 6/481; A61B 6/503; A61B 6/504; A61B 6/5211; G06T 5/20; G06T 7/0012; G06T 7/11; G06T 11/005; G06T 2207/20084; G06T 2207/30101; G06T 2211/404; G06T 2211/412;
(Continued)

(56) References Cited

U.S. PATENT DOCUMENTS

| 9,968,257 B1 * | 5/2018 | Burt ..................... A61B 5/0035 |
| 2018/0061058 A1 * | 3/2018 | Xu ....................... G06N 3/0454 |
| 2018/0061059 A1 * | 3/2018 | Xu ............................ G06T 7/11 |

(Continued)

*Primary Examiner* — Katrina R Fujita
(74) *Attorney, Agent, or Firm* — Mark M. Friedman

(57) ABSTRACT

A computer-implemented method for autonomous segmentation of contrast-filled coronary artery vessels includes receiving a CT scan volume representing a 3D volume of a region of anatomy that includes a pericardium; preprocessing the CT scan volume to output a preprocessed scan volume; converting the CT scan volume to three sets of two-dimensional slices; extracting a region of interest (ROI) by autonomous segmentation of the heart region as outlined by the pericardium, by means of three individually trained ROI extraction convolutional neural networks (CNN), each trained to process a particular one of the three sets of two-dimensional slices to output a mask denoting a heart region as delineated by the pericardium; combining the preprocessed scan volume with the mask to obtain a masked volume; converting the masked volume to three groups of sets of two-dimensional masked slices; and performing autonomous coronary vessel segmentation to output a mask denoting the coronary vessels.

6 Claims, 9 Drawing Sheets

(58) Field of Classification Search
CPC .......... G06N 3/08; G06K 9/34; G06K 9/4628; G06K 9/6274; G06K 2209/051
See application file for complete search history.

(56) References Cited

U.S. PATENT DOCUMENTS

| | | | |
|---|---|---|---|
| 2019/0192880 A1* | 6/2019 | Hibbard | A61N 5/1039 |
| 2019/0362522 A1* | 11/2019 | Han | G06T 11/00 |
| 2020/0085382 A1* | 3/2020 | Taerum | G06T 7/30 |

* cited by examiner axial plane  sagittal plane  coronal plane

AUTONOMOUS SEGMENTATION OF CONTRAST FILLED CORONARY ARTERY VESSELS ON COMPUTED TOMOGRAPHY IMAGES

TECHNICAL FIELD

The invention generally relates to autonomous segmentation of contrast filled coronary artery vessels on computed tomography images, useful in particular for the field of computer assisted diagnosis, treatment, and monitoring of coronary artery diseases.

BACKGROUND

Specialized computer systems can be used to process the CT images to develop three-dimensional models of the anatomy fragments. For this purpose, various machine learning technologies are developed, such as a convolutional neural network (CNN) that is a class of deep, feed-forward artificial neural networks. CNNs use a variation of feature detectors and/or multilayer perceptrons designed to require minimal preprocessing of input data.

SUMMARY OF THE INVENTION

So far, the image processing systems were not capable of efficiently providing autonomous segmentation of contrast filled coronary artery vessels on CT images and, therefore, Applicant has recognized a need to provide improvements in this area.

Certain embodiments disclosed herein relate to machine learning based detection of vascular structures in medical images, and more particularly, to machine learning based detection of coronary vessels in computed tomography (CT) images. Automatic detection and segmentation of contrast filled coronary arteries CT scans facilitates the diagnosis, treatment, and monitoring of coronary artery diseases.

In one aspect, there is disclosed a computer-implemented method for autonomous segmentation of contrast-filled coronary artery vessels, the method comprising:
a) receiving a CT scan volume representing a 3D volume of a region of anatomy that includes a pericardium;
b) preprocessing the CT scan volume to output a preprocessed scan volume;
c) converting the CT scan volume to three sets of two-dimensional slices, wherein the first set is arranged along the axial plane, the second set is arranged along the sagittal plane and the third set is arranged along the coronal plane;
d) extracting a region of interest by autonomous segmentation of the heart region as outlined by the pericardium, by means of three individually trained ROI extraction convolutional neural networks, each trained to process a particular one of the three sets of two-dimensional slices to output a mask denoting a heart region as delineated by the pericardium;
e) combining the preprocessed scan volume with the mask to obtain a masked volume;
f) converting the masked volume to three groups of sets of two-dimensional masked slices, wherein the first group is arranged along the axial plane, the second group is arranged along the sagittal plane and the third group is arranged along the coronal plane and each group includes at least three sets, wherein the first set corresponds to the principal plane of the set and at least two other sets are tilted with respect to the principal plane; and
g) performing autonomous coronary vessel segmentation by autonomous segmentation of the sets of the two-dimensional masked slices by means of three individually trained segmentation convolutional neural networks, each trained to process a particular one of the sets of the two-dimensional masked slices to output a mask denoting the coronary vessels.

The step of preprocessing the CT scan may include performing at least one of: windowing, filtering and normalization.

The step of preprocessing the CT scan may include computing a 3D Jerman filter response.

The method may further comprise combining the 3D Jerman filter response with the mask to obtain a masked Jerman-filtered volume, converting the masked Jerman-filtered volume to three groups of sets of two-dimensional masked Jerman-filtered slices and providing the two-dimensional masked Jerman-filtered slices as an input to a second channel of the segmentation convolutional neural networks.

The method may further comprise combining the masks denoting the coronary vessels to a segmented 3D data set representing the shape, location and size of the coronary vessels.

In another aspect, there is disclosed a computer-implemented system, comprising: at least one nontransitory processor-readable storage medium that stores at least one of processor-executable instructions or data; and at least one processor communicably coupled to the at least one non-transitory processor-readable storage medium, wherein the at least one processor is configured to perform the steps of the method in accordance with any of the embodiments described above.

These and other features, aspects and advantages of the invention will become better understood with reference to the following drawings, descriptions and claims.

BRIEF DESCRIPTION OF DRAWINGS

Various embodiments are herein described, by way of example only, with reference to the accompanying drawings, wherein.

DETAILED DESCRIPTION OF THE EMBODIMENTS

The description is not to be taken in a limiting sense, but is made merely for the purpose of illustrating the general principles of the invention.

Figure 1:
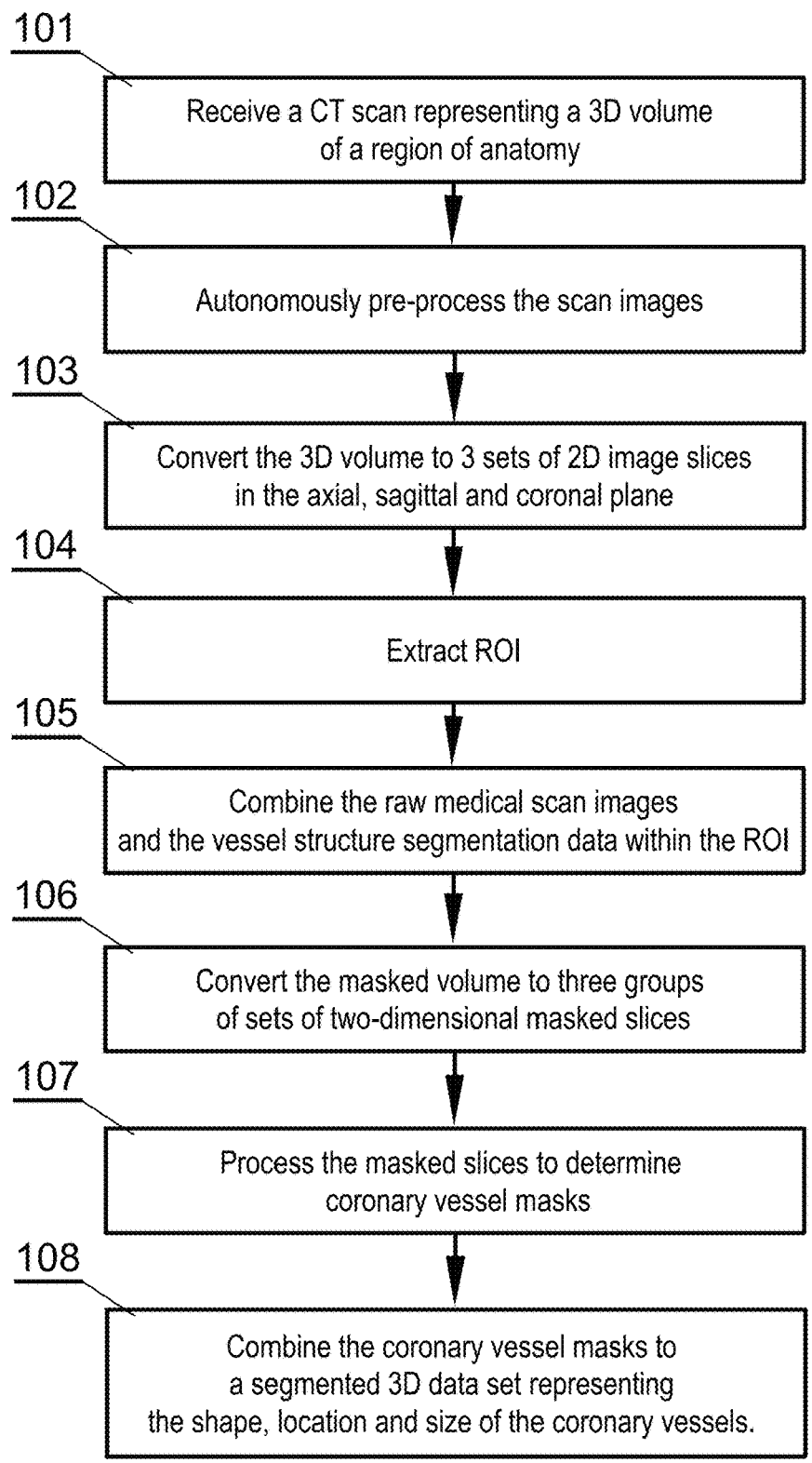
FIG. 1 shows a procedure for segmentation of the artery vessels in accordance with one embodiment.

The segmentation method in accordance with one embodiment is presented in detail in FIG. 1. In step 101, a computer tomography (CT) volumetric scan (also called a three-dimensional (3D) scan or a volume) is received. The CT volume comprises a set of medical scan images of a region of the anatomy, such as a set of DICOM (Digital Imaging and Communications in Medicine) images. The set 201 represents consecutive slices of the region of the anatomy, such as illustrated in FIG. 2A.

Figure 2A:
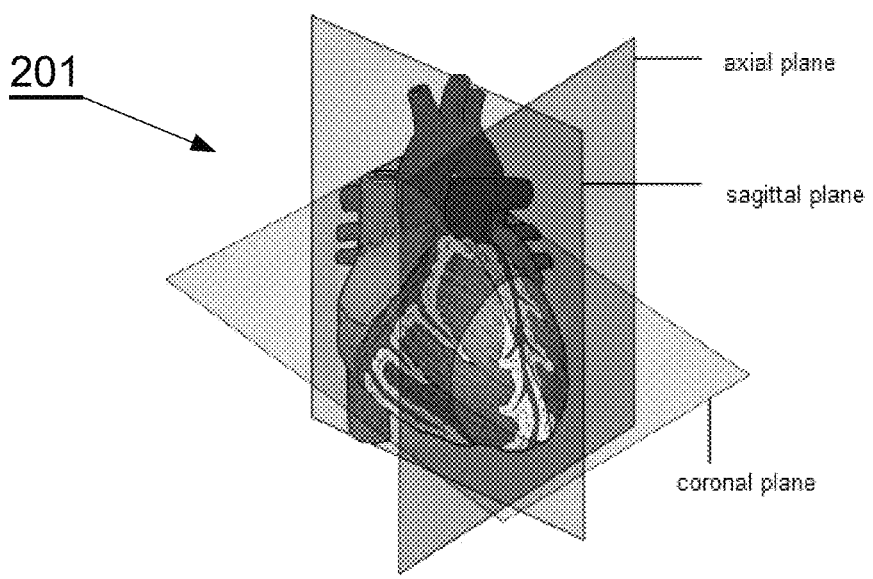
FIG. 2A shows an example of a 3D image and individual planes location in accordance with one embodiment.
Figure 2B:
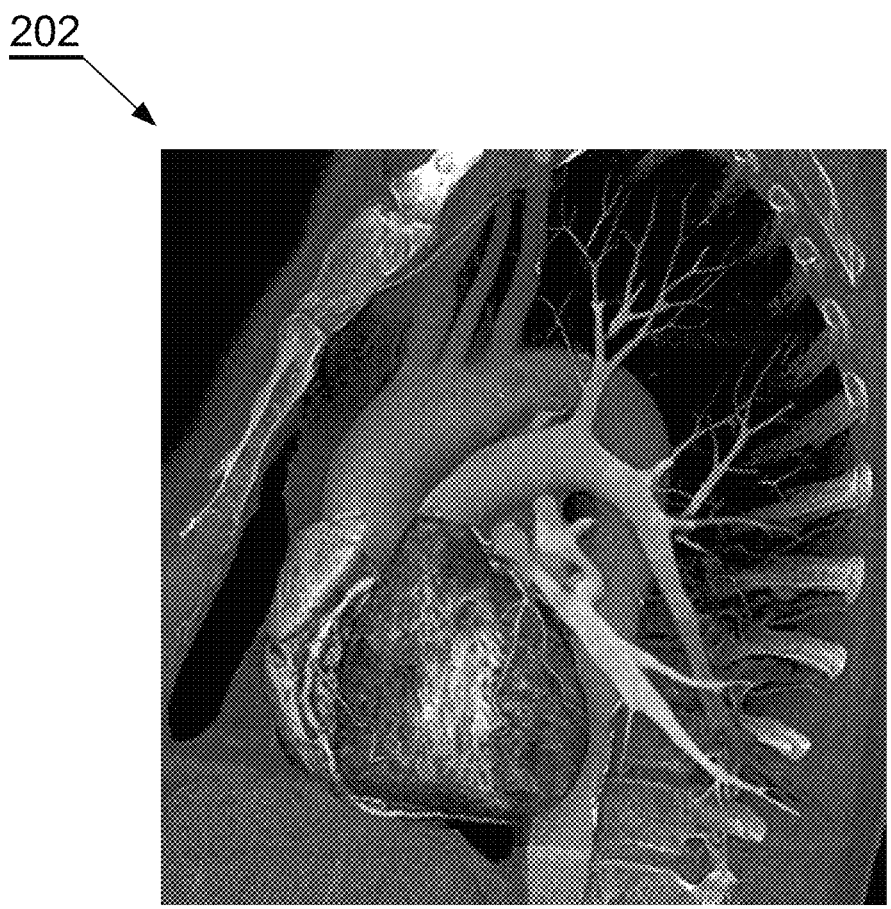
FIG. 2B shows an example of an actual image of a heart and coronary arteries in accordance with one embodiment.

The region of the anatomy should be selected such that it contains the heart and the coronary arteries 202, such as shown in FIG. 2B.

Figure 2C:
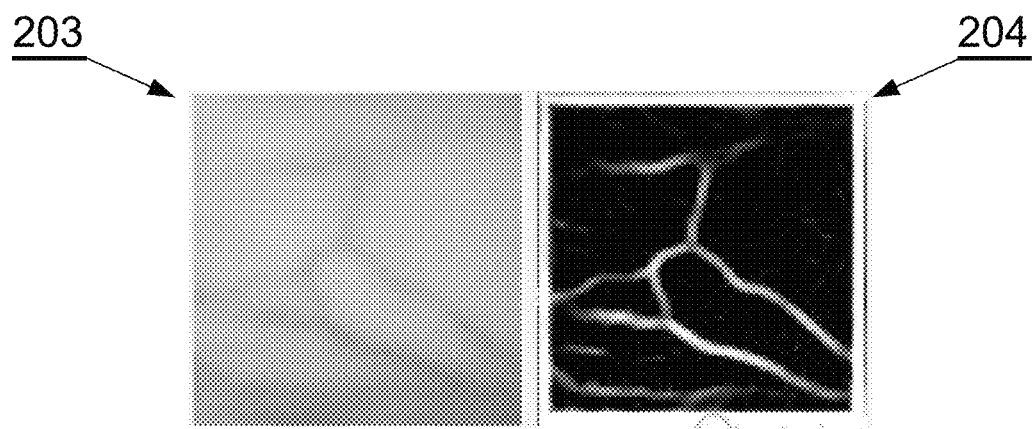
FIG. 2C shows an example of an image processed using Jerman filter in accordance with one embodiment.

In step 102, the 3D volume is autonomously preprocessed to prepare the images for region of interest (ROI) extraction. This preprocessing step may comprise raw 3D CT data windowing, filtering and normalization, as well as computing the 3D Jerman filter response for the whole volume. Computing the Jerman filter can be performed in accordance with the article "Enhancement of Vascular Structures in 3D and 2D Angiographic Images" (by T. Jerman, et al., IEEE Transactions on Medical Imaging, 35(9), p. 2107-2118 (2016)). The Jerman filter emphasizes elongated structures in images and volumes. An example of applying the filter on infrared hand vessel pattern image (left) 203 is shown in FIG. 2C, wherein the right image 204 shows the output, processed image.

Next, in accordance with certain embodiments, in step 103 the 3D volume is converted to 3 sets of two-dimensional (2D) slices, wherein the first set is arranged along the axial plane, the second set is arranged along the sagittal plane and the third set is arranged along the coronal plane (as marked in FIG. 2A).

Figure 2D:
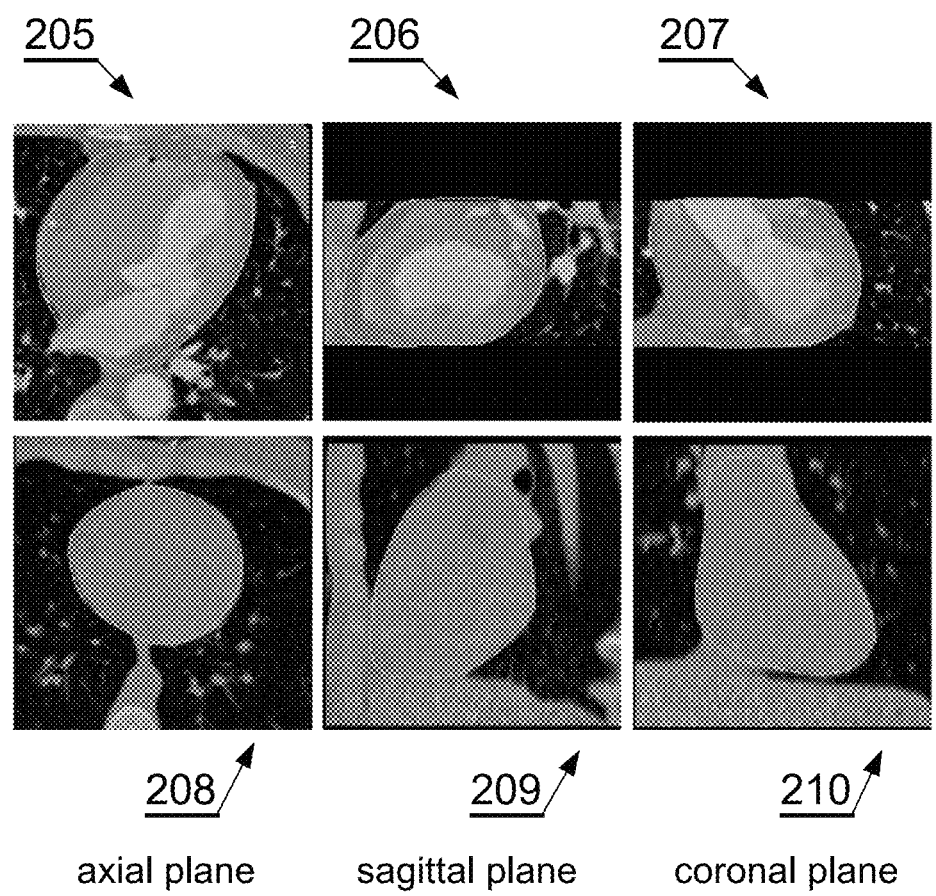
FIG. 2D shows examples of slices of the 3D image in 3 individual planes in accordance with one embodiment.

In step 104 a region of interest (ROI) is extracted by autonomous segmentation of the heart region as outlined by the pericardium. The procedure is performed by three individually trained convolutional neural networks (CNNs), each for processing a particular one of the three sets of 2D slices, namely an axial plane ROI extraction CNN, a sagittal plane ROI extraction CNN and a coronal plane ROI extraction CNN. These three CNNs are trained by training data that consists of pairs of CT volume slices in its corresponding plane and its corresponding binary, expert-annotated mask, denoting the heart region as delineated by the pericardium. Direct correspondence of binary masks and CT scan data enables their direct use for segmentation training. Sample annotations 205, 206, 207 and desired results 208, 209, 210 for the three imaging planes for two different slices in each plane are shown in FIG. 2D. The training procedure for all the three networks is identical, though each one uses a different set of data. A part of the training set is held out as a validation set.

Figure 4:
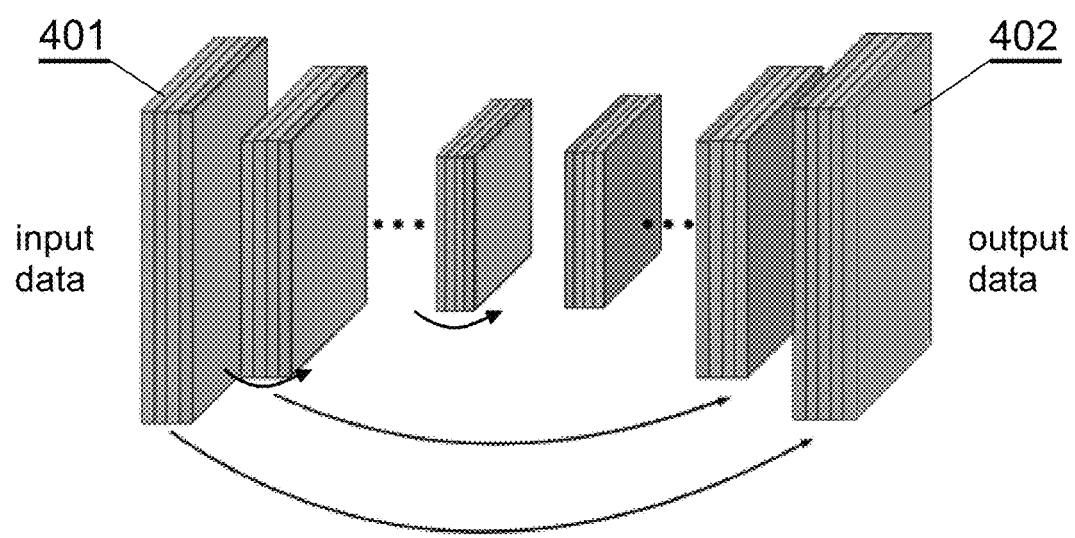
FIG. 4 shows a schematic representation of a ROI extraction CNN in accordance with one embodiment.

A schematic representation of the ROI extraction CNN in accordance with one embodiment is shown in FIG. 4. The input data represents a CT volume slice in a particular plane. The left side of the network is the encoder 401, which is a convolutional neural network, and the right side is the decoder 402. The encoder 401 may include a number of convolutional layers and a number of pooling layers, each pooling layer preceded by at least one convolutional layer. The encoder might be either pretrained, or trained from random initialisation. The decoder 402 path may include a number of convolutional layers and a number of upsampling layers, each upsampling layer preceded by at least one convolutional layer, and may include a transpose convolution operation which performs upsampling and interpolation with a learned kernel. The network may include a number of residual connections bypassing groups of layers in both the encoder and the decoder.

The residual connections may be either unit residual connections, or residual connections with trainable parameters. The residual connections can bypass one or more layers. Furthermore, there can be more than one residual connection in a section of the network. The network may include a number of skip connections connecting the encoder and the decoder section. The skip connections may be either unit connections or connections with trainable parameters. Skip connections improve the performance through information merging enabling the use of information from the encoder stages to train the deconvolution filters to upsample. The number of layers and number of filters within a layer is also subject to change, depending on the requirements of the application. The final layer for segmentation outputs a mask denoting the heart region as delineated by the pericardium (such as shown in FIG. 2D)—for example, it can be a binary mask.

The convolution layers can be of a standard kind, the dilated kind, or a combination thereof, with ReLU, leaky ReLU, Swish or Mish activation attached.

The upsampling or deconvolution layers can be of a standard kind, the dilated kind, or a combination thereof, with ReLU, leaky ReLU, Swish or Mish activation attached.

The ROI extraction CNN adjusts its internal parameters, which include the weights in the internal convolutional layers of the dimensions W×H, which denotes the width and height, respectively, with W and H being positive integers and the weights of the additional fully connected layers. During training, the network may repeatedly perform the following steps:

1. the step of prediction output binary mask based on the input CT imaging data,
2. the computation of the difference between the ground truth mask (as given in the training data) and the predicted mask with the difference computed as dice loss, cross-entropy loss, Tversky loss, . . . ;
3. The update of weights according to the gradient back-propagation method based on the steepest descent gradient algorithm or one of its variants (Adam, Nadam, adagrad, . . . )

Doing so, the network adjusts its parameters and improves its predictions over time. During training, the following means of improving the training accuracy can be used:

learning rate scheduling (fixed, cyclic learning rate changes, cosine annealing, . . . )
early stopping
regularization by dropout
L2 regularization, batch normalization, group normalization
data augmentation (by random rotations, intensity changes, noise introduction, affine and elastic transformations etc.)

The training process may include periodic check of the prediction accuracy using a held out input data set (the validation set) not included in the training data. If the check reveals that the accuracy on the validation set is better than the one achieved during the previous check, the complete neural network weights are stored for further use. The early stopping function may terminate the training if there is no improvement observed during the last CH checks. Otherwise, the training is terminated after a predefined number of steps S.

Figure 5:
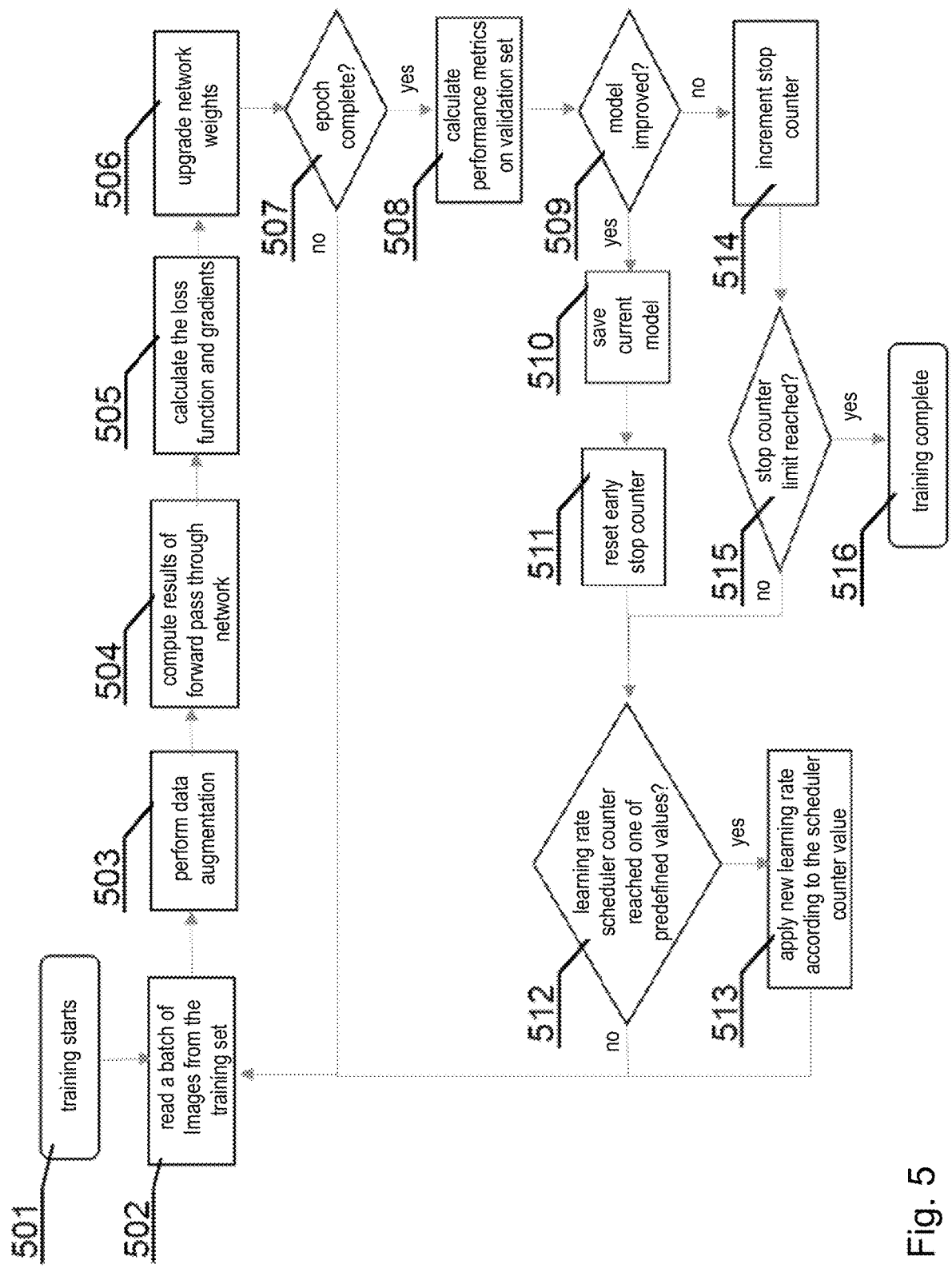
FIG. 5 shows an outline of a training procedure for the ROI extraction CNN in accordance with one embodiment.

The training procedure may be performed according to the outline shown in FIG. 5 in accordance with one embodiment. The training starts at 501. At 502, batches of training images are read from the training set, one batch at a time.

At 503 the images can be augmented. Data augmentation is performed on these images to make the training set more diverse. The input/output image pair is subjected to the same combination of transformations from the following set: rotation, scaling, movement, horizontal flip, additive noise of Gaussian and/or Poisson distribution and Gaussian blur, elastic transform, brightness shift, contrast/gamma changes, grid/optical distortion, batch-level samples averaging, random dropout, etc.

At 504, the images and generated augmented images are then passed through the layers of the CNN in a standard forward pass. The forward pass returns the results, which are then used to calculate at 505 the value of the loss function—the difference between the desired output and the actual, computed output. The difference can be expressed using a similarity metric, e.g.: mean squared error, mean average error, categorical cross-entropy or another metric.

At 506, weights are updated as per the specified optimizer and optimizer learning rate. The loss may be calculated using a per-pixel cross-entropy loss function and the Adam update rule.

The loss is also back-propagated through the network, and the gradients are computed. Based on the gradient values, the network's weights are updated. The process (beginning with the image batch read) is repeated continuously until an end of the training session is reached at 507.

Then, at 508, the performance metrics are calculated using a validation dataset—which is not explicitly used in training set. This is done in order to check at 509 whether not the model has improved. If it isn't the case, the early stop counter is incremented at 514 and it is checked at 515 if its value has reached a predefined number of epochs. If so, then the training process is complete at 516, since the model hasn't improved for many sessions now, so it can be concluded that the network started overfitting to the training data.

If the model has improved, the model is saved at 510 for further use and the early stop counter is reset at 511. As the final step in a session, learning rate scheduling can be applied. The session at which the rate is to be changed are predefined. Once one of the session numbers is reached at 512, the learning rate is set to one associated with this specific session number at 513.

Once the training is complete, the network can be used for inference, i.e. utilizing a trained model for prediction on new input data.

Upon the completion of the training, the weights of the neural network are stored and can be used for prediction. The input data for the prediction process are CT scan slices of the heart volume with contrast filled coronary arteries. For prediction of the location of the heart in individual slices in the form of the binary mask, the data is propagated through all the layers of the networks, successively, until it reaches the final layer. The output of the final layer is a binary image containing the location of the heart as delineated by the pericardium.

The individual prediction of each neural network is an image. As the network makes predictions in a slice by slice manner, the volumetric information can be reconstructed simply by stacking the slices.

The volumetric predictions in the 3 axes are then combined by averaging the individual results (e.g. calculating a sum of the components divided by the number of components) and applying a threshold and postprocessing by nonlinear filtering (morphological, median). The final result in 3D looks as shown below (a few different samples), as shown in FIG. 2D.

Next, in step 105, the preprocessed scan volume (as in FIG. 2B) and its corresponding 3d Jerman filter response (as in FIG. 2C) are additionally masked with the volumetric pericardium segmentation mask (as in FIG. 2D) with the addition of a safety margin (equal to e.g. a few voxels, preferably 3 voxels), so that all the information outside the pericardium region is cancelled out, wherein the result is a masked volume. For example, the pericardium can be post-processed with dilation using hall-shaped kernel (radius=3 voxels). This is essential, since coronary arteries occupy only a part of the overall volume. Constraining the overall volume registered by the CT scanner to the subvolume that actually contains the heart improves the accuracy of the next step (the coronary vessel segmentation).

Figure 2E:
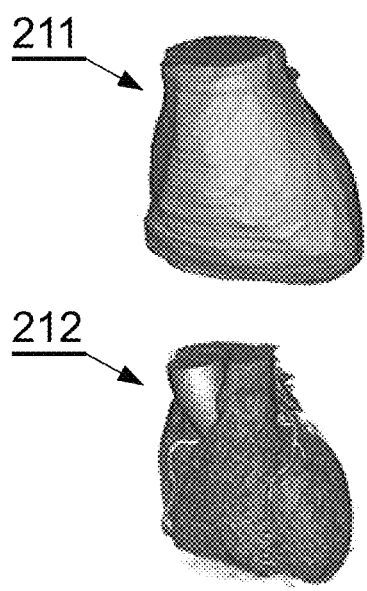
FIG. 2E shows an example of a masked raw volume in accordance with one embodiment.
Figure 2F:
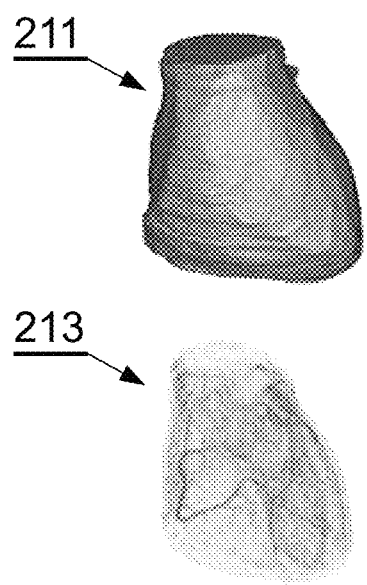
FIG. 2F shows an example of a masked volumetric Jerman filter response in accordance with one embodiment.

Both the masked raw volume (as shown in FIG. 2E—the top image 211 represents the 3D mask shape and the bottom image 212 represents the masked raw volume) and (optionally) the corresponding masked volumetric Jerman filter response 213 (as shown in FIG. 2F) are used as the input data for coronary vessel segmentation by the segmentation CNN. If the Jerman filter output is used, it is included as an additional channel of the input images.

In step 106, the masked volume is converted to three groups of two-dimensional slices, wherein each groups corresponds to a particular principal plane (the axial plane, the sagittal plane and the coronal plane) and the sets within the group correspond to planes tilted at an angle with respect to the principal plane.

Figure 6A:
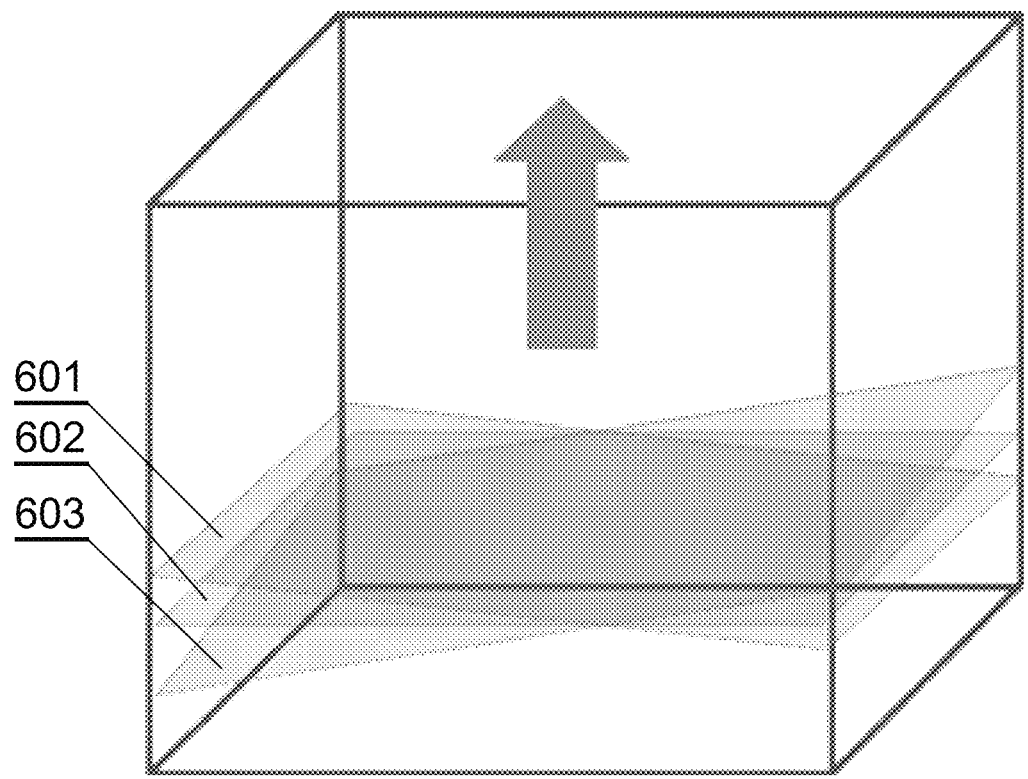
FIG. 6A shows a set of planes in accordance with one embodiment.

FIG. 6A shows three such planes 601, 602, 603, one typical, aligned with the wall of the volume (i.e. along a principal plane), and two or more additional planes, each tilted at a small angle. For example, if 2N+1 planes are used, then the angles may be +/-(N*10)—which results in for example:

for 3 planes, they are arranged at angles -10 deg., 0 deg, +10 deg.

for 5 planes, they are arranged at angles -20 deg., -10 deg., 0 deg., +10 deg., +20 deg.

Figure 6B:
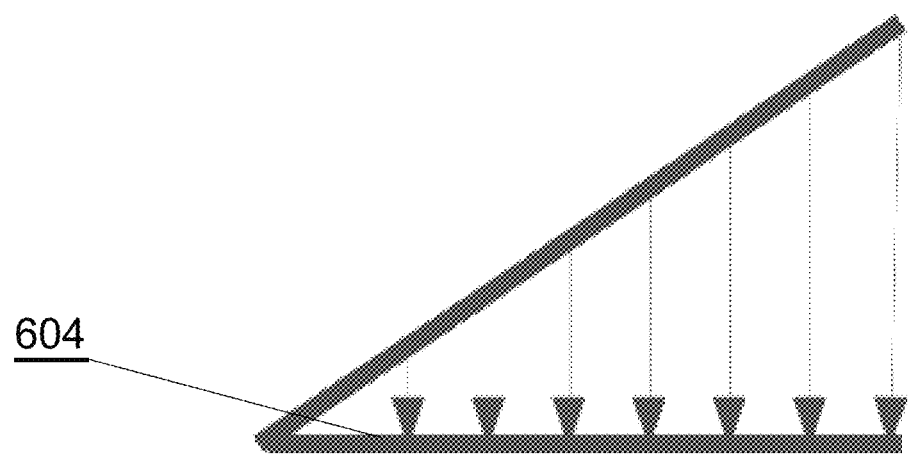
FIG. 6B shows projection of planes on a plane analogous to the regular plane in accordance with one embodiment.

Such a set of planes moves along an axis of each principal plane instead of just one, as shown in FIG. 6A. The slanted planes are projected on a plane 604 analogous to the regular plane as shown in FIG. 6B. Therefore, three groups of sets of two-dimensional slices are obtained.

Next, in step 107, the coronary vessel segmentation is performed, preferably individually for each plane, by segmentation CNNs in a similar way as for pericardium, for the two-dimensional slices obtained in the previous step. Therefore, preferably (2N+1)*3 networks are used.

Thanks to it, all the networks share the same input size and the masks do not degrade due to interpolation, since Bresenham discretization pattern is used for sampling.

Prior to use, each of the neural networks used for prediction needs to be trained. The training data consists of pairs of CT volume slices in its corresponding plane and its corresponding binary, expert-annotated mask, denoting the coronary vessels. Direct correspondence of binary masks and CT scan data enables their direct use for segmentation training.

Figure 6C:
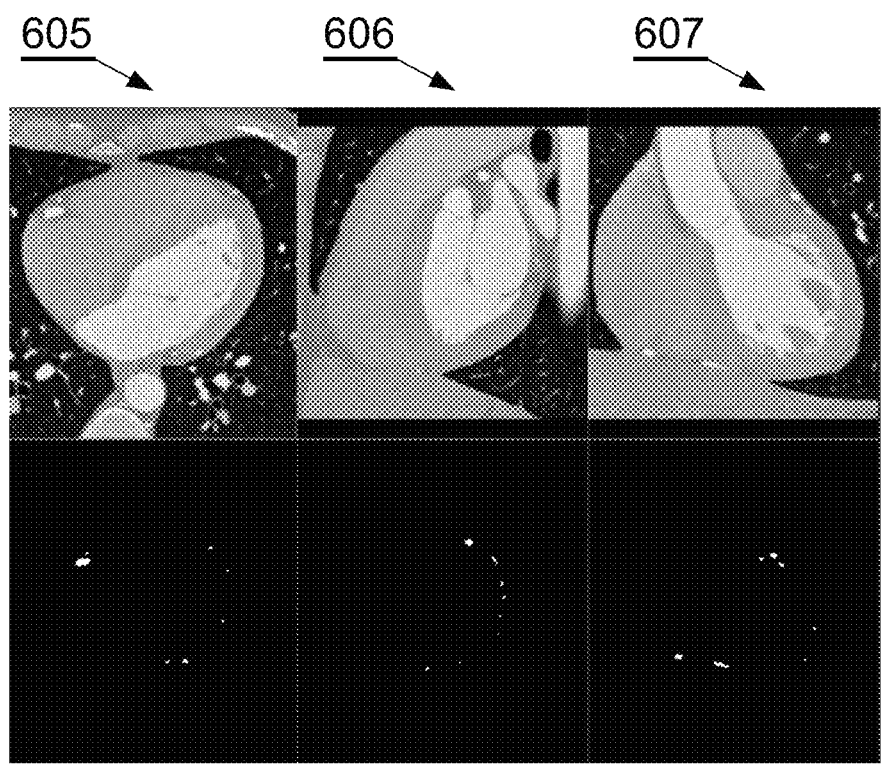
FIG. 6C shows sample annotation and desired result in accordance with one embodiment.

Sample annotation and desired result 605, 606, 607 for three imaging planes in each plane are shown in FIG. 6C—the left column 605 corresponds to the axial plane, the middle column 606 corresponds to the coronal plane and the right column 607 corresponds to the sagittal plane. The top row represents slices from the volume and the bottom row represents binary coronary vessel masks corresponding to those slices.

The training procedure for networks corresponding to the planes is identical, though each one uses a different set of data. The training is performed using a pair of corresponding CT-segmentation mask images for individual slices. A set of those forms a single batch. A part of the training set is held out as a validation set.

The segmentation CNN in accordance with one embodiment has a structure as discussed with reference to FIG. 4, with the following differences. The input data is a masked raw volume and (optionally) the corresponding masked volumetric Jerman filter response. If both types of inputs are used, then the segmentation CNNs should include an additional channel for processing that data. The output is a binary coronary vessels mask image containing the location of the coronary vessels.

Next, the coronary vessels masks output for the masked slices for the different planes can be combined to a segmented 3D data set representing the shape, location and size of the coronary vessels.

The training procedure in accordance with one embodiment is equivalent to that discussed in FIG. 5. Upon the completion of the training, the weights of the neural network are stored and can be used for prediction. The input data for the prediction process are CT scan slices of the heart volume with contrast filled coronary arteries masked with the heart region as predicted in the previous steps. For prediction of the location of the coronary vessels slices in the form of the binary mask, the data is propagated through all the layers of the networks, successively, until it reaches the final layer. The output of the final layer is a binary image containing the location of the coronary vessels. The individual prediction of each neural network is an image. As the network makes predictions in a slice by slice manner, we can reconstruct the volumetric information simply by accumulating the response from all the networks slice by slice in all directions. The volumetric predictions are then combined by averaging the individual results and applying a threshold or other means (majority voting, reconstruction neural network, e.g. 3D Unet).

Figure 3:
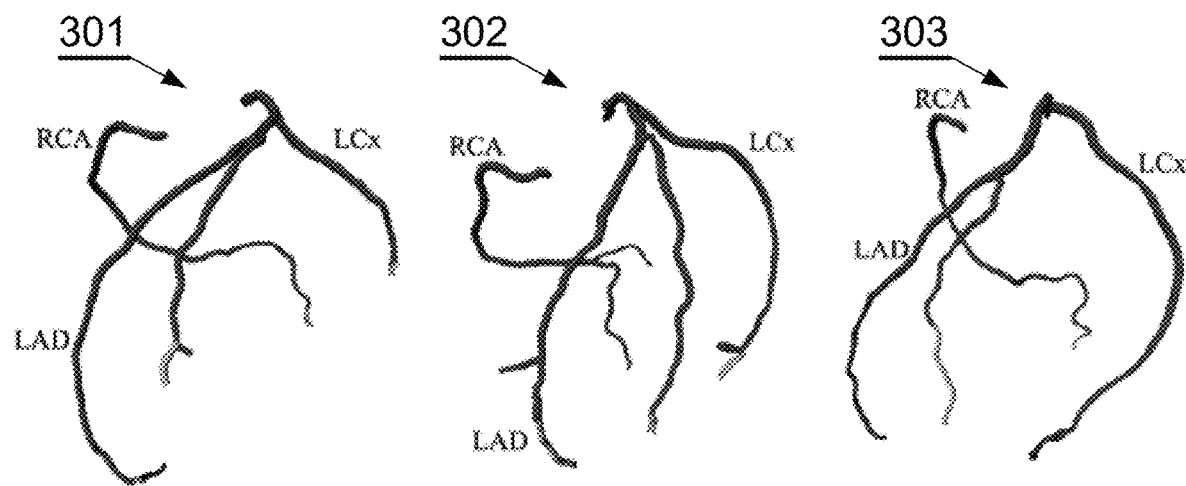
FIG. 3 shows examples of final results in accordance with one embodiment.

The predicted binary volume representing the coronary vessels can be subjected to additional post-processing:
  Deletion of small blobs to minimize the number of false positive responses
  Frangi/Jerman/median/morphological filtering to improve the smoothness and continuity of segmented vessels
  Transformation of volumetric data into surface mesh for visualization of volumetric mesh for further processing using e.g. finite element method for mechanical modeling
Examples of desired final results 301, 302, 303 are given in FIG. 3.

Figure 7:
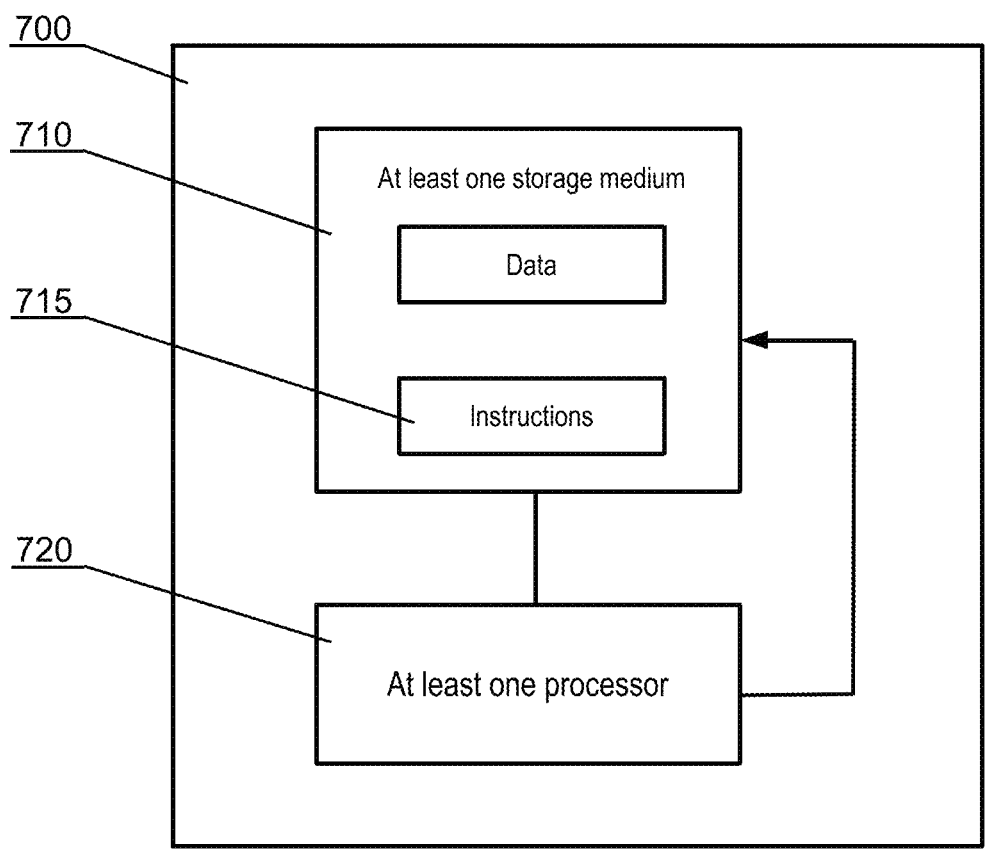
FIG. 7 shows the structure of a computer system for implementing the method of FIG. 1 in accordance with one embodiment.

The functionality described herein in accordance with one embodiment can be implemented in a computer system 700, such as shown in FIG. 7. The system 700 may include at least one nontransitory processor-readable storage medium 710 that stores at least one of processor-executable instructions 715 or data; and at least one processor 720 communicably coupled to the at least one nontransitory processor-readable storage medium 710. The at least one processor 720 may be configured to (by executing the instructions 715) perform the procedure of FIG. 1.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A computer-implemented method for autonomous segmentation of contrast-filled coronary artery vessels, the method comprising:
  a) receiving a CT scan volume representing a 3D volume of a region of anatomy that includes a pericardium;
  b) preprocessing the CT scan volume to output a preprocessed scan volume;
  c) converting the CT scan volume to three sets of two-dimensional slices, wherein the first set is arranged along the axial plane, the second set is arranged along the sagittal plane and the third set is arranged along the coronal plane;
  d) extracting a region of interest (ROI) by autonomous segmentation of the heart region as outlined by the pericardium, by means of three individually trained ROI extraction convolutional neural networks (CNN), each trained to process a particular one of the three sets of two-dimensional slices to output a mask denoting a heart region as delineated by the pericardium;
  e) combining the preprocessed scan volume with the mask to obtain a masked volume;
  f) converting the masked volume to three groups of sets of two-dimensional masked slices, wherein the first group is arranged along the axial plane, the second group is arranged along the sagittal plane and the third group is arranged along the coronal plane and each group includes at least three sets, wherein the first set corresponds to the principal plane of the set and at least two other sets are tilted with respect to the principal plane; and
  g) performing autonomous coronary vessel segmentation by autonomous segmentation of the sets of the two-dimensional masked slices by means of three individually trained segmentation convolutional neural networks (CNN), each trained to process a particular one of the sets of the two-dimensional masked slices to output a mask denoting the coronary vessels.

2. The method according to claim 1, wherein the step of preprocessing the CT scan includes performing at least one of: windowing, filtering and normalization.

3. The method according to claim 1, wherein the step of preprocessing the CT scan includes computing a 3D Jerman filter response.

4. The method according to claim 3, further comprising combining the 3D Jerman filter response with the mask to obtain a masked Jerman-filtered volume, converting the masked Jerman-filtered volume to three groups of sets of two-dimensional masked Jerman-filtered slices and providing the two-dimensional masked Jerman-filtered slices as an input to a second channel of the segmentation convolutional neural networks (CNN).

5. The method according to claim 1, further comprising combining the masks denoting the coronary vessel to a segmented 3D data set representing the shape, location and size of the coronary vessels.

6. A computer-implemented system, comprising:
at least one nontransitory processor-readable storage medium that stores at least one of processor-executable instructions or data; and
at least one processor communicably coupled to the at least one nontransitory processor-readable storage medium, wherein the at least one processor is configured to perform the steps of the method of claim 1.

* * * * *